United States Patent [19]

Sawai et al.

[11] Patent Number: 4,985,356

[45] Date of Patent: Jan. 15, 1991

[54] CLONING OF DNA ENCODING HUMAN MOTILIN PRECURSOR AND EXPRESSION OF THE PRECURSOR

[75] Inventors: Kiichi Sawai, Aichi; Jun Takeda, Kyoto; Yutaka Seino, Amagasaki; Hiroo Imura, Kyoto; Kenichi Tanaka, Nagoya; Haruo Takahashi, Nagoya; Takahiko Mitani, Nagoya; Masayasu Kurono, Nagoya, all of Japan

[73] Assignee: Sanwa Kagaku Kenkyusho Co., Ltd., Aichi, Japan

[21] Appl. No.: 190,849

[22] Filed: May 6, 1988

[30] Foreign Application Priority Data

May 7, 1987 [JP] Japan ................. 62-109757

[51] Int. Cl.$^5$ .............. C12P 21/00; C12P 19/34; C12Q 1/68; C12N 15/00
[52] U.S. Cl. ........................... 435/69.4; 435/6; 435/91; 435/69.1; 435/69.7; 435/69.8; 435/172.3; 435/320; 435/252.33; 536/27; 935/11; 935/13; 935/18
[58] Field of Search ............... 435/68, 70, 172.3, 320, 435/6, 91, 69.1, 69.4, 69.7, 69.8; 935/11, 13, 18; 536/27

[56] References Cited

PUBLICATIONS

Okayama and Berg, *Mol. Cell. Biol.*, vol. 2, pp. 161–170, 1982.
Seino et al., *FEBS. Lett.*, vol. 223(1), pp. 74–76, Oct. 1987, "Sequence of an Intestinal cDNA Encoding Human Motilin Precursor".
Poitras et al., *Regulatory Peptides*, vol. 5, pp. 197–208, 1983.
Suggs et al., *Proc. Natl. Acad. Sci.*, vol. 178(11), pp. 6613–6617, Nov. 1981, "Use of Synthetic Oligonucleotides as Hybridization Probes: Isolation of Cloned cDNA Sequences for Humans for $\beta_2$-Microglobulin".
Ohtsuka et al., *J. Biol. Chem.*, vol. 260, pp. 2605–2608, 1985.
Brown, J. C. et al., "Gastroenterology", vol. 6, pp. 401–404, (1974).
"Can. J. Biochem.", vol. 52, pp. 7–8, (1974), Schubert et al.
"Gastroenterology", vol. 80, pp. 456–460, (1981).

*Primary Examiner*—Robin L. Teskin
*Attorney, Agent, or Firm*—Armstrong, Nikaido, Marmelstein, Kubovcik & Murray

[57] ABSTRACT

A cloned single-strand DNA comprising nucleotide sequence which encodes human motilin precursor, a cloned double-strand DNA consisting of the single-strand DNA and its complementary single-strand DNA, a fragment of the single- or double-strand DNA, a plasmid, in which the double-strand DNA or its fragment is integrated, as well as a process for the preparation of the single- or double-strand DNA.

6 Claims, 3 Drawing Sheets

FIG. 2

```
5'---  AGACAAGTAGAGAGAACTCCTCCAGAGACCCACTCAGAGCTGCACGCCCTCCAAG
            -50       -40       -30       -20       -10      -1

ATGGTATCCCGTAAGGCTGTGGCTGCTCGCTGGTGGTGCATGTAGCTGCCATGCTGGCCTCCCAGACGGAAGCCTTCGTCCCATCTTC
MetValSerArgLysAlaValAlaAlaLeuLeuValValHisValAlaAlaMetLeuAlaSerGlnThrGlnThrGluAlaPheValProIlePhe
 1        10        20        30        40        50        60        70        80        90
 1                                         10                  20                      30

ACCTATGGCGAACTCCAGAGGATGCAGGAAAAAGGAATAAAGGCAAAAGAAATCCCTGAGTGTATGGCAGAGGTCTGGGAGGAA
ThrTyrGlyGluLeuGlnArgMetGlnGluLysGlyAsnLysGlyLysGluIleProGluValTrpGlnArgSerGlyGluGlu
            100       110       120       130       140       150       160       170       180
                                    40                      50                          60

GGTCCTGTAGACCCTGCGGAGCCCATCGGGAAGAAGAAAACGAAATGATCAAGCTGACTGCTCCTCTGGAAATTGGAATGAGGATGAAC
GlyProValAspProAlaGluProIleArgGluGluGluLeuAsnGluMetIleLysLeuThrAlaProLeuGluIleGlyMetArgMetAsn
  190       200       210       220       230       240       250       260       270
              70                        80                          90

TCCAGACAGCTGGAAAAGTACCCGGCCACCCTGGAAGGCTGCTGAGTGCTTCCCCAGCATGCAGAGATGCTTCCCCAGCATGCAGCCAAGTGATGGCCACGCTGG
SerArgGlnLeuGluLysTyrProAlaThrLeuGluGlyLeuLeuSerGlyMetLeuProGlnHisAlaAlaLys***
  280       290       300       310       320       330       340       350       360
                              100                         110

GGAGAAGGTGGACAGATTTGGGAGGCCCTCCTGCCCAAGTGAGGCCCTGGGAATTACAGAGCTGCCAGCTGGGCTTGGAAGGAAAAC
   370       380       390       400       410       420       430       440       450

ACCTTTCCAAAGCAAATTCCCCCTCCAGCAAATAAAGCATGAAATATACAG   ---3'
   460       470       480       490       500
```

CLONING OF DNA ENCODING HUMAN MOTILIN PRECURSOR AND EXPRESSION OF THE PRECURSOR

BACKGROUND OF THE INVENTION

1. Field of the Invention

The present invention relates to motilin and more particularly to a cloned single-stranded DNA, (hereinafter simply refer to as single-strand DNA) comprising nucleotide sequence which encodes human motilin precursor, a cloned double-stranded DNA, (hereinafter simply refer to as double-strand DNA) consisting of the single-strand DNA and its complementary single-strand DNA, a fragment of the single- or double-strand DNA, and a plasmid, in which the double-strand DNA or its fragment is integrated, as well as a process for the preparation of the single- or double-strand DNA.

2. Related Arts

The motilin is one of peptide hormones, first isolated from mucous membrane of porcine upper small intestine and determined its amino acid sequence by Brown, J. C. et al ["Gastroenterology" Vol. 62, pages 401–404 (1972) and "Can. J. Biochem." Vol. 52, pages 7–8 (1974)].

The porcine motilin disclosed in such literatures is one extracted from the animal tissue, consists of 22 amino acids and has molecular weight of about 2700. It has been well known that the porcine motilin has a hypermotility action of digestive tract and contracting action of gastroduodenal and colonic smooth muscle therein, as physiological actions. As the hypermotility action, it has been reported that a staying period of time in stomach is shortened ["Gastroenterology" Vol. 80, pages 456–460 (1981)] and as the contracting action of smooth muscle in the digestive tract, it has been known that the motilin shows a strong contracting action to rabbit and human gastrantestinal tract, independent from a neuro system. Therefore, it has been considered that the motilin is useful for curing gastrointeropathies at the period of post-operation and for diagnosis thereof.

The motilin according to the prior arts has been obtained through extraction from porcine organ and thus it was quite difficult to obtain the same in a large amount. Further, a structure of human motilin has not yet been determined. Namely, the motilin has not actually been applied for clinical use, due to its poor productivity, in spite of that an effectiveness thereof as the agent for curing gastro-enteropathy has been expected.

SUMMARY OF THE INVENTION

A basic object of the invention lies in developing an industrially acceptable process for the preparation of human motilin and its related substances, by utilizing so-called —Bio-Technologies—.

A principal object of the invention is to provide a cloned DNA comprising a human motilin precursor, or a fragment thereof.

An additional object of the invention is to provide a process for the preparation of the cloned DNA encoding the human motilin precursor, or the fragment thereof.

A further object of the invention is to provide a plasmid, wherein the cloned DNA or its fragment, for instance the human motilin per se or another physiologically or biologically active portion in the human motilin precursor, is integrated, so that a micro-organism or animal cell transformed by such plasmid expresses the human motilin or other biologically active substances to allow a large scale production thereof.

The inventors have carefully studied and investigated to finally obtain the cloned DNA for the human motilin precursor and determine its structure, whereby the basic object has been attained.

According to the invention, the principal object is attained by a cloned single-strand DNA comprising about 550 nucleotides which encodes therein an amino acid sequence for human motilin precursor.

The DNA according to the invention has the following nucleotide sequence or any other nucleotide sequence same with the former in biological view point.

```
5'-ATG GTA TCC CGT AAG GCT GTG GCT GCT CTG CTG GTG GTG CAT GTA
   GCT GCC ATG CTG GCC TCC CAG ACG GAA GCC TTC GTC CCC ATC TTC
   ACC TAT GGC GAA CTC CAG AGG ATG CAG GAA AAG GAA CGG AAT AAA
   GGG CAA AAG AAA TCC CTG AGT GTA TGG CAG AGG TCT GGG GAG GAA
   GGT CCT GTA GAC CCT GCG GAG CCC ATC AGG GAA GAA GAA AAC GAA
   ATG ATC AAG CTG ACT GCT CCT CTG GAA ATT GGA ATG AGG ATG AAC
   TCC AGA CAG CTG GAA AAG TAC CCG GCC ACC CTG GAA GGG CTG CTG
   AGT GAG ATG CTT CCC CAG CAT GCA GCC AAG-3'
``` wherein A, C, G and T are, respectively, a oligodeoxyribonucleotide having adenine, cytosine, guanine or thymine base and said sequence is given as that of each codon corresponding to a specified amino acid.

The term of —nucleotide sequence same in biological view point—means a case of that even if, kinds or arrangement of nucleotides constituting codons, as —TTA— and —CTG— are different but each codon designates same amino acid (in the exemplar case, each of the codons designates same amino acid of —leucine). In this case, therefore, the term means various nucleotide sequences encoding the following amino acid sequence which is designated by the nucleotide sequence shown hereinabove.

```
Met—Val—Ser—Arg—Lys—Ala—Val—Ala—Ala—Leu—Leu—Val—Val—His—Val—
Ala—Ala—Met—Leu—Ala—Ser—Gln—Thr—Glu—Ala—Phe—Val—Pro—Ile—Phe—
Thr—Tyr—Gly—Glu—Leu—Gln—Arg—Met—Gln—Glu—Lys—Glu—Arg—Asn—Lys—
Gly—Gln—Lys—Lys—Ser—Leu—Ser—Val—Trp—Gln—Arg—Ser—Gly—Glu—Glu—
Gly—Pro—Val—Asp—Pro—Ala—Glu—Pro—Ile—Arg—Glu—Glu—Glu—Asn—Glu—
Met—Ile—Lys—Leu—Thr—Ala—Pro—Leu—Glu—Ile—Gly—Met—Arg—Met—Asn—
Ser—Arg—Gln—Leu—Glu—Lys—Tyr—Pro—Ala—Thr—Leu—Glu—Gly—Leu—Leu—
Ser—Glu—Met—Leu—Pro—Gln—His—Ala—Ala—Lys
```

According to the DNA for human motilin precursor having said nucleotide and amino acid sequences, it is found that the human motilin is encoded in a region of the 26th to 47th counting from methionine (Met) residue designated by the initiation codon of ATG and partitioned at both ends by alanine (Ala) residue designated by the codon of GCC and lysine (Lys) residue designated by the codon of AAG. It can be considered that the firstly arranged about 25 amino acids beginning from the initiative Met are those corresponding to a signal peptide which concerns to secretion, in view of its structure.

According to a process of the invention, the cloned double-strand DNA encoding human motilin precursor can be prepared by converting RNA extracted from upper small intestine (duodenum) into poly(A)RNA, constructing cDNA library with use of the poly-(A)RNA and vector/primer DNA to carry out a transformation of *Escherichia coli* (*E. coli*), while previously synthesizing a mixture of 24 tricosamers, each consisting of 23 origodeoxyribonucleotides of the formula

(A)

wherein I is inosine and employed for the position in the nucleotide sequence, where any of A, G, T and C possibly occupies, which is complementary to mRNA corresponding to Phe-Val-Pro-Ile-Phe-thr-Tyr-Gly of 1st to 8th amino acids from N-terminal in known amino acid sequence for porcine motilin, labeling each synthesized oligodeoxyribonucleotide shown by said formula (A) at N-terminal, screening said transformed *E. coli* by a hybridization with use of said labeled oligodeoxyribonucleotides as probes to obtain a positive clone which hybridize with the probes.

The ground that the 1st to 8th amino acids from N-terminal in the amino acids for porcine motilin is selected for the oligodeoxyribonucleotide (A) as the probe and that inosine is employed in each position, where any of A, G, T and C may occupies, lies in making possible to respond also to the case that there is some difference in sequence between porcine and human motilins, and to be minimum kinds of mRNA corresponding to such amino acids.

A cloned single-strand DNA encoding human motilin can be prepared by denaturing the resulting cloned double-strand DNA with use of a method known per se, for instance treating same at 90° C. for about 3 minutes and then cooling in an ice bath.

The cloned single- or double-strand DNA encoding human motilin precursor can be made into a fragment or fragments of various length, by treating same with a suitable restriction enzyme(s), binding fragments, synthesizing a region not obtaining through the cleaving technique and binding the synthesized region to the cleaved fragment to make the desired fragment of human motilin region only or another region showing a physiological or biological activity.

Moreover, the cloned double-strand DNA encoding human motilin precursor or any fragment thereof may be integrated into a plasmid with a technique known per se, for instance taking out a plasmid from *E. coli*, purifying the plasmid, treating the plasmid with a restriction enzyme to cut the same at a specified base position, and ligating with a DNA ligase the cloned DNA to the cleavage site of the cut plasmid to re-construct a plasmid with the recombinant DNA.

The human motilin precursor, human motilin per se or other biologically active substance(s) can be prepared in a large amount by transforming a microorganism or eukaryotic cell with the plasmid integrated therein the double-strand DNA or a fragment thereof and culturing the microorganism or eukaryotic cell. Further, the DNA fragment encoding an amino acid sequence other than that for motilin may also be employed for investigating novel biologically active substance(s).

BRIEF DESCRIPTION OF THE DRAWING

FIG. 2 shows a determined nucleotide sequence of cloned cDNA encoding human motilin precursor as well as an amino acid sequence corresponding to the nucleotide sequence in the human motilin precursor region.

DETAILED DESCRIPTION OF THE PREFERRED EMBODIMENTS

Figure 1:
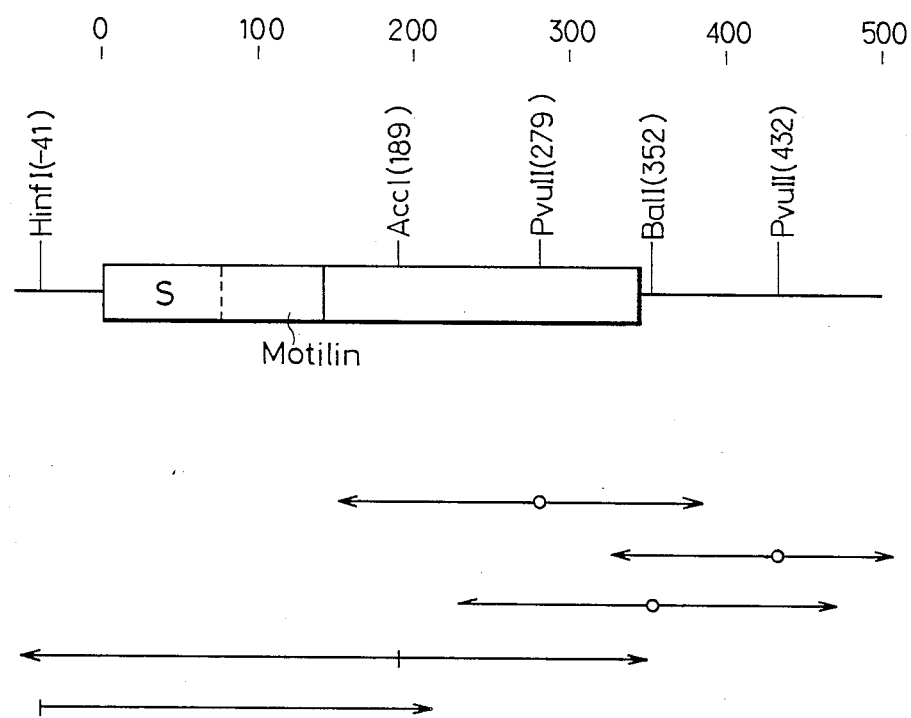
FIG. 1 is an illustration showing cDNA region comprising cloned human motilin precursor in accordance with the invention, as well as a strategy and a restrction enzyme map for determining a nucleotide sequence in the human motilin precursor region.

The invention will now be further explained with reference to Examples for preparing a cloned human motilin precursor and a plasmid integrating the precursor therein, respectively as well as a Test Example for determining a structure of the precursor.

EXAMPLE 1

(a) Preparation of poly(A)RNA Comprising mRNA of Human Motilin

It has been known through a radio immunoassay and others that porcine motilin presents at an upper small intestine and other organs ["Scand. J. Gastroenterol." Vol. 11, pages 47–52 (1976)]. Therefore, a human duodinum obtained from a patient during pancreatoduodenectomy for pancreatic cancer was treated, in accordance with the method as disclosed by Chirgwin, J. M. et al ["Biochemistry" Vol. 18, pages 5294–5299 (1979)]. Namely, the total RNA (1.2 mg) was extracted from the tissue by 4M-guanidium thiocyanate, bonded to an oligo(dT)cellulose column with use of 10 mM-Tris hydrochloride buffer containing 0.5M-KCl, as a binding buffer, and eluted with use of a buffer free from KCl to obtain about 150 μg of the desired poly(A)RNA.

It has been confirmed through an electrophoresis that this RNA is not degraded, in view of RNA bands at 18s and 28s.

(b) Synthesis of Oligodeoxyribonucleotides Complementary to mRNA Which Corresponds to an Amino Acid Sequence for Human Motilin A mixture of 24 tricosamers, each consisting of 23 deoxyribonucleotides of the formula

(A)

wherein I is inosine and employed for the position in the nucleotide sequence, where any of A, G, T and C possibly occupies, which is complementary to mRNA corresponding to Phe-Val-Pro-Ile-Phe-thr-Tyr-Gly of 1st to 8th amino acids from N-terminal in known amino acid sequence for porcine motilin were synthesized with use of a DNA synthesizer marketed as —Gene Assembler— from Pharmacia, Sweden, it is to be noted that these oligodeoxyribonucleotides include all of possible mRNA sequences corresponding to said amino acid sequence.

(c) Construction of cDNA Library

A cDNA library was constructed with use of about 30 μg of said poly(A)RNA and 4.3 μg of vector/primer DNA and in accordance with the method disclosed by Okayama, H and Berg, P. ["Mol. Cell. Biol." Vol. 2, pages 161–170 (1982)] and E. coli (HB101 strain) was transformed in accordance with the method disclosed by Morrison, D. A. ["Methods in Enzymol." Vol. 68, pages 326–331, (1979)]. Through a screening with use of LB-agar plate containing 50 μg/ml of ampicillin, ampicillin resistant transformants were obtained by 10,000 cells per 1 μg of poly(A)RNA, namely 300,000 cells in total.

(d) cDNA Cloning

The cloning was carried out in accordance with the method as disclosed by Hanahan, D. et al ["Gene" Vol. 10, pages 63–67 (1980)].

Namely, about 50000 cells among said about 300,000 ampicillin resistant transformants as described in said Item (c) were replicated on nitrocellulose filter, cultured for 3 to 4 hours on a agar plate containing 50 μg/ml of ampicillin and transferred on LB-agar plate containing 500 μg/ml of chloramphenicol to further culture the same at 37° C. for one overnight. A colony formed on the filter was subjected to bacteriolysis by treatment of 0.5N sodium hydroxide for 5 minutes, namely a double-strand DNA was made into a single-strand DNA, fixed on a plate, neutralized to make pH to 7.5 and dipped the filter for 5 minutes in Tris hydrochloride buffer (pH 7.5) containing 1.5M-NaCl to remove bacterial fragments and the like other than DNA. Thereafter, the filter was air dried and baked for 2 hours at 80° C. to obtain a testing filter for screening.

While, the screening of the transformants was carried out as follows, in accordance with the method as disclosed by Grunstein, M. et al ["Proc. Natl. Acad. Sci. U.S.A." Vol. 72, pages 3961–3965 (1975)].

Namely, each of the oligodeoxyribonucleotides synthesized by the method as stated in said Item (b) and shown by said formula (A) was labeled at 5'-end with [γ-$^{32}$P]ATP (Amersham, 5,000 Ci/mmol) and T4-polynucleotide kinase (Toyobo Co., Ltd., Osaka, Japan) to make the same into probe for screening. A relative activity of each probe was $1-2\times 10^6$ cpm/pmol.

The transformants on the testing filter were screened by a hybridization at 50° C. and with use of the probes (labeled oligodeoxyribonucleotides) and judged by a conventional autoradiogram method to find that only one transformant among about 50,000 transformants is hybridizing positive clone.

This positive clone, namely that comprising human motilin precursor was analized by an electrophoresis to find that it has cDNA insert region of about 650 bp including poly(dA)(dT) tails and poly(dG)(dC) tracts. This cloned DNA is double-strand one and nucleotide sequence thereof had been elucidated as disclosed in the Test Example to be stated below. Therefore, the DNA can be made into a fragment(s) in various length, by treating same with a suitable restriction enzyme(s) and if necessary, binding a synthetic DNA to the fragment to obtain a desired DNA fragment consisting of the motilin precursor region, motilin region only or other region showing a certain biological activity.

Further, the double-strand DNA in full length, fragment or piece thereof can be made into corresponding single-strand one by treating same at 90° C. for about 3 minutes and then ice cooling to cause a denaturation thereof.

TEST EXAMPLE

Determination of Nucleotide Sequence for Cloned Human Motilin Precursor and Corresponding Amino Acid Sequence A nucleotide sequence of cDNA insert region for the cloned human motilin precursor obtained in Example 1 was determined by sub-cloning to a pUC19 plasmid, in accordance with the method disclosed by Maxam, A. M. et al ["Methods in Enzymol." Vol. 65, pages 499–560 (1980)] and the dideoxy method disclosed by Hattori, M. et al ["Anal. Biochem." Vol. 152, pages 232–238 (1980)], who employs a modified plasmid.

In FIG. 1, there are given a cDNA region of the cloned human motilin precursor, restriction enzymes selected for determining a nucleotide sequence in the region and a strategy for sequencing the cloned cDNA. The numerals at uppermost portion in the Figure are nucleotide number given as from the human motilin precursor region boxed at intermediate portion. The —PvuII— and the like are names of the restriction enzymes as selected and a numeral given in parentheses shows the numbers indicating the 5'-terminal nucleotide generated by cleavage. Among the boxed region for the human motilin precursor, a region (S) shows putative signal peptides, and another region (Motilin) shows that to be estimated as corresponding to human motilin per se. In the lower portion in FIG. 1, each of horizontal arrow shows a direction and limit of the nucleotide sequence to be determined, due to the respective restriction enzyme. Each of the determination results obtained in accordance with the method disclosed by Maxam A. M. et al is shown by an arrow with a short vertical line which shows an isotope labeled position at 5'-terminal. While, each determination results obtained in accordance with the method disclosed by Hattori, M. et al is shown by adding a small circle at an end of the arrow which indicates a starting position for nucleotide sequencing.

In FIG. 2, there are given thus determined nucleotide sequence of the cloned cDNA encoding the human motilin precursor as well as the amino acid sequence corresponding to the nucleotide sequence in the human motilin precursor region. In the Figure, the numeral given at upper side is number of nucleotides similar to FIG. 1 and another numeral given at lower side is number of amino acid residues in the human motilin precursor region. The region boxed with a solid line shows the putative motilin region, and the region boxed with broken line shows the location of the oligonucleotide probe for screening the transformants in Example 1.

As seen from FIG. 2, the human motilin precursor region lies as an open reading frame beginning from the initiation codon of ATG and ending by the terminal codon of TGA, which comprises therein the nucleotide sequence encoding the amino acid sequence same with the known porcine motilin. As boxed with the solid line, the nucleotide sequence occupies such a position in the amino acid number counting from first methionine (Met) as from 26th phenylalanine (Phe) to 47th glutamine (Gln). The beginning portion in the human motilin precursor region, namely the 1st Met to 25th Ala seems to be a signal sequence (S region in FIG. 1) which may generally be found on secretory proteins, in view of its structure consisting of relatively hydrophobic amino acids as from 6th Ala to 25th Ala. In view of that end portion in the motilin region is partitioned by neighboring two lysines (Lys) of basic amino acid, it seems to be that the motilin will be secreted in the form of the precursor and then cleaved by a protease in blood or the like to form the mature motilin.

EXAMPLE 2

Preparation of Plasmid Integrating Human Motilin Precursor

This example will be explained with reference to the Figures and more particularly FIG. 3. In the first place, the cloned cDNA for the human motilin precursor as shown in FIGS. 1 and 2 was treated with restriction enzymes of *Hinfl* and *Ball* to obtain a fragment of about 490 bp. On the other hand, *Nhel* and *Xhol* linkers were prepared with use of a DNA synthesizer marketed by Pharmacia, Sweden. The linkers were joined to the *Hinfl* and *Ball* sites of the fragment, respectively.

While, a commercially available plasmid (—pMSG— marketed by Pharmacia, Sweden) was treated with the restriction enzymes of *Nhel* and *Xhol*. To the resulting ends of the plasmid fragment, said fragment with linkers was joined to re-construct into a plasmid, in which human motilin precursor is integrated.

Figure 3:
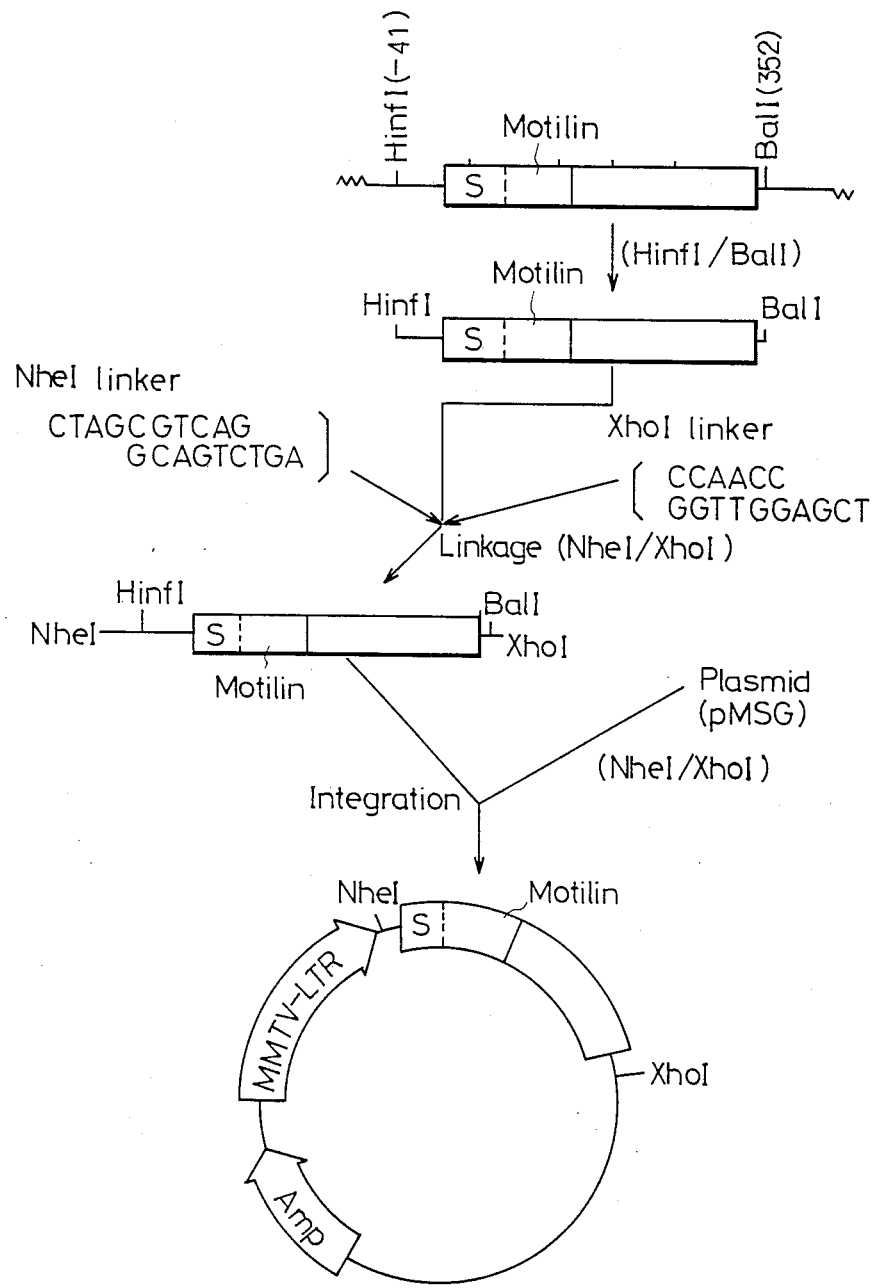
FIG. 3 is an illustration showing steps to prepare a plasmid wherein the human motilin is integrated.

As shown in the last portion in FIG. 3, the resulting plasmid has DNA clone of the human motilin precursor at down-stream of a powerful promoter of a long terminal repeat on mouse mammary tumor virus (MMTV-LTR). If L or CHO cells are transformed in a conventional manner but with use of such plasmid and cultured same, therefore, the human motilin can be prepared in a large amount.

What is claimed is:

1. A cloned double-stranded DNA having a single strand of DNA comprising about 550 nucleotide sequences encoding a human motilin precursor.

2. A cloned double-stranded DNA according to claim 1, wherein said DNA has a nucleotide sequence of 5'-ATG GTA TCC CGT AAG GCT GTG GCT GCT CTG CTG GTG GTG CAT GTA
GCT GCC ATG CTG GCC TCC CAG ACG GAA GCC TTC GTC CCC ATC TTC
ACC TAT GGC GAA CTC CAG AGG ATG CAG GAA AAG GAA CGG AAT AAA
GGG CAA AAG AAA TCC CTG AGT GTA TGG CAG AGG TCT GGG GAG GAA
GGT CCT GTA GAC CCT GCG GAG CCC ATC AGG GAA GAA GAA AAC GAA
ATG ATC AAG CTG ACT GCT CCT CTG GAA ATT GGA ATG AGG ATG AAC
TCC AGA CAG CTG GAA AAG TAC CCG GCC ACC CTG GAA GGG CTG CTG
AGT GAG ATG CTT CCC CAG CAT GCA GCC AAG-3'

3. A cloned double-stranded DNA which encodes the amino acid sequence consisting essentially of Met—Val—Ser—Arg—Lys—Ala—Val—Ala—Ala—Leu—Leu—Val—Val—His—Val—
Ala—Ala—Met—Leu—Ala—Ser—Gln—Thr—Glu—Ala—Phe—Val—Pro—Ile—Phe—
Thr—Tyr—Gly—Glu—Leu—Gln—Arg—Met—Gln—Glu—Lys—Glu—Arg—Asn—Lys—
Gly—Gln—Lys—Lys—Ser—Leu—Ser—Val—Trp—Gln—Arg—Ser—Gly—Glu—Glu—
Gly—Pro—Val—Asp—Pro—Ala—Glu—Pro—Ile—Arg—Glu—Glu—Glu—Asn—Glu—
Met—Ile—Lys—Leu—Thr—Ala—Pro—Leu—Glu—Ile—Gly—Met—Arg—Met—Asn—
Ser—Arg—Gln—Leu—Glu—Lys—Tyr—Pro—Ala—Thr—Leu—Glu—Gly—Leu—Leu—
Ser—Glu—Met—Leu—Pro—Gln—His—Ala—Ala—Lys.

4. A double-stranded DNA according to claim 3 wherein said DNA is a human double-stranded DNA.

5. A plasmid comprising a double-stranded DNA having a single strand of 550 nucleotides which encode therein an amino acid sequence consisting essentially of Met—Val—Ser—Arg—Lys—Ala—Val—Ala—Ala—Leu—Leu—Val—Val—His—Val—
Ala—Ala—Met—Leu—Ala—Ser—Gln—Thr—Glu—Ala—Phe—Val—Pro—Ile—Phe—
Thr—Tyr—Gly—Glu—Leu—Gln—Arg—Met—Gln—Glu—Lys—Glu—Arg—Asn—Lys—
Gly—Gln—Lys—Lys—Ser—Leu—Ser—Val—Trp—Gln—Arg—Ser—Gly—Glu—Glu—
Gly—Pro—Val—Asp—Pro—Ala—Glu—Pro—Ile—Arg—Glu—Glu—Glu—Asn—Glu—
Met—Ile—Lys—Leu—Thr—Ala—Pro—Leu—Glu—Ile—Gly—Met—Arg—Met—Asn—
Ser—Arg—Gln—Leu—Glu—Lys—Tyr—Pro—Ala—Thr—Leu—Glu—Gly—Leu—Leu—
Ser—Glu—Met—Leu—Pro—Gln—His—Ala—Ala—Lys.

6. A process for the preparation of a cloned double-stranded DNA having a single strand comprising about 550 nucleotides coding for human motilin precursor, which comprises steps of converting mRNA extracted from human small intestine into poly(A)RNA, constructing a cDNA library from said poly(A)RNA and vector/primer DNA, transforming colonies of *Escherichia coli* with said cDNA library, screening said transformants with synthetic, labeled probes comprising a mixture of 24 tricosamers, each consisting of 23 deoxyribonucleotides of the formula

wherein I is inosine and each tricosamer is complementary to mRNA coding for

Phe-Val-Pro-Ile-Phe-Thr-Tyr-Gly of the 1st to 8th amino acid sequence from N-terminal of the amino acid sequence of motilin, labeling each synthesized oligodeoxyribonucleotide shown by said formula (A) at its terminal, screening said transformed *Escherichia coli* by picking clones which hybridize with said probes, and optionally denaturing the double-stranded DNA into the single-stranded DNA.